United States Patent [19]

Fleche

[11] Patent Number: 5,831,043
[45] Date of Patent: Nov. 3, 1998

[54] PROCESS FOR THE OXIDATION OF SUGARS

[75] Inventor: Guy Fleche, Hazebrouck, France

[73] Assignee: Roquette Freres, Lestrem, France

[21] Appl. No.: 769,050

[22] Filed: Dec. 18, 1996

[30] Foreign Application Priority Data

Dec. 21, 1995 [FR] France .................................. 95 15269

[51] Int. Cl.⁶ .............................. C07H 3/04; C07H 3/06; C07H 1/00; C08B 37/00
[52] U.S. Cl. .................... 536/18.5; 536/123.12; 536/124
[58] Field of Search .................. 536/18.5, 124, 536/123.12

[56] References Cited

U.S. PATENT DOCUMENTS 5,334,756  8/1994  Likibi et al. ............................ 562/565

FOREIGN PATENT DOCUMENTS 0 532 370  3/1992  European Pat. Off. .
WO 95/07303  3/1995  WIPO .

OTHER PUBLICATIONS

Moore, Walter J. Physical Chemistry. Third Edition. Prentice–Hall, Englewood Cliffs, NJ. (1962), pp. 273–274.

*Primary Examiner*—Gary L. Kunz
*Attorney, Agent, or Firm*—Henderson & Sturm

[57] ABSTRACT

The invention relates to an improved process for the alkaline oxidation in aqueous medium of sugars possessing one or a number of primary alcohol functional groups using hypohalites and in the presence of a catalyst composed of a binary or tertiary alkyl nitroxyl.

The process is noteworthy in that the oxidation takes place in the presence of high concentrations of sugars.

The products obtained by the process, some of which are novel, can be used as builders in detergent compositions.

9 Claims, No Drawings

PROCESS FOR THE OXIDATION OF SUGARS

The invention relates to a process for the oxidation of sugars.

More precisely, this invention relates to a process for the oxidation of sugars by a hypohalite using a catalyst composed of a binary or tertiary alkyl nitroxyl.

It is known that sugars, and more generally their derivatives, can be oxidized in alkaline medium using hypohalites in the presence of a catalyst composed of a binary or tertiary alkyl nitroxyl.

This oxidation is reflected by the appearance of carboxylic acid functional groups in place of the primary alcohol functional groups and also of the terminal hemiacetal functional group of small glucose polymers, for example.

Such a process has been described in International Patent Application WO 95/07303. This process, in which methyl glucosides, a disaccharide, such as trehalose, and polysaccharides, such as starch, inulin and pullulan, were given as examples, can also be applied to β-glucans, such as cellulose, curdlan or scleroglucan, and is also applicable to hydrolysates or to derivatives of these sugars.

Starch or inulin, or their hydrolysates, can be oxidized by this process to poly-α-glucuronic acids or poly-β-fructuronic acids. To do this, an aqueous alkaline solution containing approximately 7 to 15 grams of sugar on a dry basis per liter of water, treated with an oxidation catalyst composed of approximately 0.1 to 2.5% of 2,2,6,6-tetramethylpiperidin-1-oxyl (hereinafter known as TEMPO) and of 20% to 75% of sodium bromide as cooxidizing agent, these percentages being expressed with respect to the sugar, is subjected to the effect of bleach acting as oxidizing agent.

This International Patent Application WO 95/07303 also teaches that, in order to be effective, such an oxidation reaction must take place at a temperature of less than 30° C. and that it is highly preferable to carry out this oxidation at a temperature of between 0° and 5° C.

Under these conditions, it is indicated that it is possible to obtain, for example, starches which are oxidized to levels close to the theoretical maximum, namely that virtually all the anhydroglucosyl units of these polymers are converted to anhydroglucuronyl units. The hemiacetal terminal reducing ends of the glucose or of the glucose oligomers are also oxidized to carboxylic acid functional groups, thus constituting a glucaric acid or glucuronyl glucarates, unless these ends are protected, for example, by methylation. This last oxidation, affecting the non-protected reducing ends, is, according to the teaching of the patent application in question, only true for starch or inulin hydrolysates of low molecular weight.

It has been found, and it is this which is above all at the basis of the present invention, that oxidation levels which are just as high could be obtained, whatever the sugar to be oxidized, if aqueous solutions of sugars or of their polymers containing much more than 15 grams of sugar per liter of water were used.

Firstly, the present invention thus relates to a process for the alkaline oxidation, in aqueous medium, of sugars possessing one or a number of primary alcohol functional groups using hypohalites and in the presence of a catalyst composed of a binary or tertiary alkyl nitroxyl, characterized in that the concentration of sugars in the aqueous medium is greater than 50 g/l, preferably greater than 100 g/l and more preferentially still greater than 200 g/l.

A solution of polyglucuronic acids is thus obtained in the case of the oxidation of glucose polymers.

In the case of the oxidation of aldose monomers, the aldaric acids corresponding to the monomer subjected to oxidation are thus obtained.

The Applicant Company has discovered that, surprisingly, the complete oxidation of sugars which is obtained by the catalysed oxidation by a binary or tertiary alkyl nitroxyl, in alkaline medium, using hypohalites, could be ensured even if the concentration of sugars in the reaction mixture was considerably greater than 15 g/l.

Sugars can be oxidized with concentrations ranging up to 500 g/l and even more. The Applicant Company has discovered that, indeed, it is in particular problems of solubility or of viscosity which limit the concentrations at which the oxidations according to the process of the invention can be carried out.

It is possible, for example, to oxidize substances of low molecular weight, such as xylose, arabinose, glucose, fructose, mannitol, sorbitol, lactose, lactitol, maltitol, starch hydrolysates, and the like, at concentrations considerably greater than 100 g/l.

In addition, the Applicant Company has also noticed that such an oxidation could also be carried out at temperatures considerably greater than 30° C., even ranging up to 60° C. These high temperatures make it possible to increase the solubility limit of the sugars and to lower the viscosity of their solutions, thus making it possible to further increase their concentration.

It is thus possible to oxidize, for example at 40° C., solutions containing more than 200 g/l of mannitol even though, at a temperature of 0° C., the solubility limit of mannitol would be greatly exceeded.

Insofar as it is desired to oxidize sugars of polymeric nature, such as starch, inulin, cellulose, pectins, gums or their hydrolysates or the products deriving therefrom by esterification, etherification, cross-linking, and the like, the concentration limit of the solutions to be oxidized will be that of the constraints imposed by the viscosity of these solutions.

However, this limit will increase as the temperature of the reaction mixture increases.

Secondly, the process according to the invention is thus characterized in that the oxidation is carried out at a temperature greater than 30° C., preferably greater than 40° C.

As the levels of oxidation, as well as the selectivity of the oxidation with respect to the primary alcohols or the hemiacetal functional groups, remain substantially the same in the process of the invention as in the process of the prior art represented essentially by Patent Application WO 95/07303, it is obvious that the increase in the concentrations of the sugars to be oxidized according to the process of the present invention results in a considerable saving as regards the volume of the reactors necessary for implementing the process of the invention.

Moreover, the fact of operating at high temperatures makes it possible to dispense with the use of extremely expensive refrigerating units. The heat given off by these highly exothermic oxidation reactions, which increases as the mixtures become more concentrated, can be discharged simply by the use of water at ambient temperature.

Finally, the Applicant Company has noticed that another advantage of the high temperatures, in all cases equal to or greater than 30° C., was that the rates of oxidation of the sugars were thereby found to be increased and that it thus became possible to decrease the levels of catalysts, in particular the levels of TEMPO.

This considerable increase in the efficiency of the catalyst at high temperature means, at least as regards the oxidation of sugars of low molecular mass, that it becomes possible to considerably reduce, indeed even to dispense with, the expensive cocatalyst, which is sodium bromide, employed in the process of the prior art.

The selectivity of the oxidation is found to be only very slightly affected thereby and only traces of oxidation affecting secondary alcohols are thus recorded.

On the other hand, this considerable increase in the efficiency of the catalyst makes it possible, unlike that which was taught in Patent WO 95/07303, also to oxidize the hemiacetal ends of glucose polymers with a degree of polymerization greater than 15 and virtually to suppress the reducing power of the starch hydrolysates subjected to the oxidation.

To the knowledge of the Applicant Company, such products, composed of glucuronyl glucarates containing less than 0.5% of reducing sugars, do not exist.

It will have been understood that the term sugar(s) employed in the present invention here encompasses oses, uloses or ketoses, alditols and all the compounds which derive therefrom, such as aldonic, ketoaldonic and uronic acids or polyacids, their acetylated, aminated, alkylated, carboxymethylated and cationized derivatives, and the like, and the homogeneous or heterogeneous polymers of these sugars, should these sugars carry at least one primary alcohol functional group.

The process of the invention proves to be, for example, particularly effective with respect to starch hydrolysates and starch hydrolysates hydrogenated or oxidized by other processes and the products which may be obtained by the process behave very advantageously in detergent compositions, due to their complexing properties conferred by the many carboxyl functional groups which they carry.

Other oxidizable materials which can be used in the process of this invention can also be composed of primary alcohols containing a hydrocarbon chain, such as methanol, ethanol, propanol, and the like, insofar as the latter are soluble in water at the preferred temperatures of the process of the invention.

In order to implement the process of the invention, the sugar is therefore dissolved in water in order to obtain a concentration of at least 50 g/l.

It is essential, in the process of the invention, for the oxidation to take place in alkaline medium.

The preferred pH for bringing the oxidation reaction of the process of the invention to a successful conclusion is from approximately 9 to 13. The appearance of acid functional groups as the oxidation reaction progresses of course necessitates the introduction of an alkali continuously into the reaction mixture in order to maintain this pH.

Patent U.S. Pat. No. 5,334,756 relates to a process for the preparation of carboxylates, in particular alkyl polyglucosides, which comprises the subjection of an alkyl polyglucoside containing primary hydroxyl groups to a controlled oxidation, but in weakly alkaline medium, since the pH is between 8.0 and 9.0 and preferably between 8.5 and 9.0.

According to the process of the invention, the oxidation is carried out in the presence of a catalyst composed of a binary or tertiary alkyl nitroxyl capable of releasing a nitrosonium cation which is reduced to hydroxylamine when a primary alcohol functional group is oxidized to carboxylic acid. This nitrosonium cation is regenerated in situ by an oxidizing agent which conveniently comprises a hypochlorite.

In a preferred embodiment of the invention, the catalyst consists of 2,2,6,6-tetramethylpiperidin-1-oxyl or TEMPO and the hypochlorite is bleach.

The catalyst can be added to the water either before or after the addition of the sugar.

The concentration of the catalyst must be at least 0.01% with respect to the weight of sugar. It can decrease as the working temperature increases. However, it is preferable to employ TEMPO concentrations of between 0.05% and 1.5%. The more the concentration of catalyst increases, the more the reaction time decreases. The reverse is obviously true.

The reaction temperature, according to the process of the invention, is at least 30° C.

Oxidation products of excellent quality, containing only a few percent of material resulting from oxidations of secondary alcohols, are obtained at temperatures ranging up to approximately 60° C. or even slightly higher.

These non-selective oxidations increase as the temperature rises.

The time period required for the oxidation depends, simultaneously, on the temperature, the pH and the percentage of the catalyst. Surprisingly, the concentration of sugar in the reaction mixture has little effect. Generally, the desired levels of oxidation, which can be between 10% and 100% and more generally between 60 and 99% of the primary alcohol functional groups to be oxidized, are obtained in approximately 1 minute to approximately 2 hours, although, depending on the circumstances and depending on the way the oxidation reactors have been fitted out (stirring, design of the heat exchangers), it is possible to carry out the oxidations over longer times.

Thus, the time period required for the oxidation is much less than that taught by Patent U.S. Pat. No. 5,334,756.

When, for example, low levels of catalysts or the lowest temperatures are employed, a longer oxidation time can be envisaged.

More or less heavy polymers, should they carry primary alcohol functional groups, can be used in the process of the invention.

However, the Applicant Company has noticed that, in order to oxidize sugars of relatively low molecular mass, such as, for example, monomers, dimers and polymers of simple sugars having a degree of polymerization of less than approximately 20, it was not necessary to use a cooxidizing agent. This is in contrast with the teaching of the prior art.

A process for the alkaline oxidation of monomers, dimers and polymers of simple sugars having a degree of polymerization of less than approximately 20 according to the invention thus comprises the use of only bleach, without the addition of an expensive cooxidizing agent, such as sodium bromide.

The oxidation of maltitol, which is a dimer composed of glucose and sorbitol bonded at $\alpha, 1 \rightarrow 4$, is for example possible by the action of bleach alone without addition of bromide.

Glucuronyl-$\alpha(1\rightarrow 4)$-glucaric acid, which is a novel product and which exhibits very advantageous sequestering properties, is thus obtained with a quantitative yield.

The oxidation of maltitol could take place, for example, according to the process of the invention at a temperature of 40° C., with a TEMPO level of 1.3% and at a maltitol concentration in the syrup subjected to the oxidation of 25%, without bromide.

Generally, for all the primary alcohol functional groups of a sugar to be oxidized, it is preferable to employ a slight excess of oxidizing agent, i.e. approximately 2.2 mol of NaOCl per mole of primary alcohol to be oxidized, i.e., for example, 6.6 mol of NaOCl per mole of maltitol to be oxidized, as maltitol has three primary alcohol functional groups.

However, the Applicant Company has noticed that glucose syrups or maltodextrins with a DE greater than 2 could be oxidized virtually quantitatively without addition of cocatalysts, should they be oxidized at a temperature greater than 30° C.

The process of the present invention has at least four advantages with respect to the process provided in Patent Application WO 95/07303, in which the oxidation of the sugars takes place in very dilute and very cold medium.

Firstly, the levels of catalysts can be lowered, as has already been said.

Secondly, it is not necessary to use cocatalysts, at least when products of low molecular mass are being oxidized.

Thirdly, it is not necessary to resort to the use of refrigerating units.

Fourthly, it is not necessary to evaporate large amounts of water in order to recover the products obtained by the process of the present invention.

In the process of the present invention, it is preferable to gradually add alkali to the reaction mixture, in order to keep the pH of this mixture constant.

It might also be possible to introduce all at once, at the beginning of the reaction, the total amount of alkali considered necessary for the completion of the reaction.

The sugar and the oxidizing agent, or the oxidizing agent/cooxidizing agent mixture, can be introduced continuously into the reactor but it is preferable to have them all dissolved in the water from the beginning of the reaction.

When the oxidation reaction is complete or when it has reached the threshold which had been set for it and which is a function of the relative amount of oxidizing agent employed, it is found that the alkali consumption has ceased or the pH has stabilized, if all the alkali has been introduced all at once at the beginning of the reaction.

The catalyst can then be removed from the reaction mixture, for example by carrying out a solvent extraction, but it is also possible, on a more practical level, to adsorb it on a column of granular activated charcoal.

After filtration, the reaction mixture, thus rid of its catalyst and charcoal fines, can be treated by chromatographic ion exclusion techniques or by membranes, so as to remove the inorganic salts therefrom.

If there is need of it, these reaction mixtures, thus purified, can be concentrated and dried. It is also possible to subject them to crystallization in order to isolate pure products therefrom when pure sugars have been subjected to the oxidation.

Other details of the invention will become apparent on reading the following examples. In these examples, the sugar concentrations are given as percentage by weight of sugars with respect to the weight of sugar-containing solutions employed. The percentages of catalysts are given by weight with respect to the weight of dry sugars employed.

EXAMPLE 1

A 50% by weight aqueous sorbitol solution is prepared by addition of 100 grams of sorbitol to 100 ml of demineralized water in a stirred and thermostatically controlled reactor equipped with a pH measuring probe. This solution is brought to 45° C. and then 0.8 g of TEMPO and 1.15 l of bleach with a chlorimetric value of 48°, in the form of a solution diluted beforehand to 10% and adjusted to pH 10.4 with hydrochloric acid, are added thereto.

The reaction is allowed to take place at a temperature of 45° C. with water passing through the jacket of the reactor at 20° C. and while continuously adding a 10% sodium hydroxide solution thereto, so as to maintain the pH at 10.4.

After 20 minutes, it is found that sodium hydroxide consumption has become virtually zero.

The contents of the reactor are then percolated through a column of granular activated charcoal and then this column is eluted with water, so as to remove the catalyst therefrom.

Analysis of the product obtained shows that the mixture contains, on a dry basis:

33% of glucaric acid in the form of its sodium salt,

67% of sodium chloride.

Products from the overoxidation of glucaric acid are not detected.

EXAMPLE 2

A 25% by weight aqueous mannitol solution is prepared in the same reactor by addition of 100 grams of mannitol to 300 ml of demineralized water.

This solution is brought to 55° C. and then 1 g of TEMPO and 1.15 l of bleach with a chlorimetric value of 48°, in the form of a solution diluted beforehand to 25% and adjusted to pH 10.6 with hydrochloric acid, are added thereto.

The reaction is allowed to take place at a temperature of 55° C. with water passing through the jacket of the reactor at 20° C. and while continuously adding a 10% sodium hydroxide solution thereto, so as to maintain the pH at 10.6.

After 30 minutes, it is found that sodium hydroxide consumption has become virtually zero. The contents of the reactor are then percolated through a column of granular activated charcoal, so as to remove the catalyst therefrom, and then this column is eluted with water. 7 liters of solution are collected containing:

1.9% of mannaric acid in the form of its sodium salt, 4.1% of sodium chloride.

Traces of products from the overoxidation of mannaric acid are detected.

EXAMPLE 3

A 50% by weight aqueous maltitol solution is prepared in the same reactor by addition of 100 grams of maltitol to 100 ml of demineralized water.

This solution is brought to 35° C. and then 0.3% of TEMPO and 0.9 l of bleach with a chlorimetric value of 48°, in the form of a solution diluted beforehand to 10% and adjusted to pH 10.4 with hydrochloric acid, are added thereto.

The reaction is allowed to take place at a temperature of 45° C. with water passing through the jacket of the reactor at 20° C. and while continuously adding a 25% sodium hydroxide solution, so as to maintain the pH at 10.4.

After 40 minutes, it is found that sodium hydroxide consumption has become virtually zero.

The contents of the reactor are then percolated through a column of granular activated charcoal, so as to remove the catalyst therefrom, and then this column is eluted with water.

Analysis of the product obtained shows that the mixture contains:

37% of glucuronyl glucaric acid in the form of its sodium salt,

63% of sodium chloride.

Products from the overoxidation of glucuronyl glucaric acid are not detected.

The salt present in the crude reaction product was removed by a chromatographic ion exclusion technique on a strong cationic resin.

A product was thus obtained which only assays 4% of sodium chloride. The complexing power of the glucuronyl glucaric acid, thus purified, was measured by potentiometry with a calcium electrode and a value of 16 mg of complexed calcium per gram of glucuronyl glucaric acid in the form of its sodium salt was measured, allowing excellent behaviour as builder in the formulation of detergent compositions to be predicted for this product.

EXAMPLE 4

A 20% aqueous Glucidex® 19 solution, corresponding to a dry matter of 100 g, is prepared in the same reactor again. This product is a maltodextrin sold by the Applicant Company which is obtained by hydrolysis of starch with α-amylase.

This solution is brought to 35° C. and then 1 g of TEMPO and 0.75 l of bleach with a chlorimetric value of 48°, in the form of a solution diluted beforehand to 50% and adjusted to pH 10.3 with hydrochloric acid, are added thereto.

The operation is allowed to take place at a temperature of 35° C. while continuously adding a 10% sodium hydroxide solution thereto, so as to maintain the pH at 10.3.

After 120 minutes, it is found that sodium hydroxide consumption has become virtually zero.

The contents of the reactor are then percolated through a column of granular activated charcoal and then this column is eluted with water.

Analysis of the product obtained shows that the mixture contains:

45% of glucaric, glucuronyl glucaric and polyglucuronyl glucaric acids in the form of their sodium salts, 55% of sodium chloride.

It has a mean degree of polymerization of approximately 5 and its content of free reducing sugars, measured by the Bertrand method, is 0.3%, indicating that, under the specific conditions of the process of the invention, even the hemiacetal functional groups of glucose polymers with a degree of polymerization greater than 20 are oxidized, despite the absence of cooxidizing agent.

EXAMPLE 5

2995 grams of water and 1591 grams of sodium hydroxide are introduced into a Biolaffite trade mark fermenter with a glass vessel, with a working volume of 20 liters, in order to form 4586 grams of a 34.7% sodium hydroxide solution.

55 grams of sodium anthraquinone-2-monosulphonate and 18.2 ml of 110-volume hydrogen peroxide are then added to this sodium hydroxide solution.

The fermenter is then aerated with an air flow of 20 liters per minute and with stirring at a rate of 1000 revolutions per minute.

After having stirred this mixture at 25° C. for 30 minutes, the temperature is brought to 45° C. 18,344 grams of a glucose syrup obtained by acid hydrolysis of maize starch, exhibiting a dry matter content of 50% and a DE of 37 (mean degree of polymerization equal to 2.7), are then added slowly and evenly over 3 hours 30 minutes.

The temperature is then set at 55° C. and stirring and aeration are continued for 2 hours 30 minutes. The content of reducing sugars in the reaction mixture has then fallen to 0.3 g/100 g of glucose syrup on a dry basis (it was 37 g/100 g at the beginning).

After having corrected the pH of this reaction mixture to 7, it is percolated through a column of granular activated charcoal, so as to remove the sodium salt of anthraquinone-2-monosulphonic acid therefrom.

This alkaline oxidative degradation reaction converts the glucose syrup, composed of polyglucosylglucose, to polyglucosyl arabinonate.

All of this polyglucosyl arabinonate syrup is introduced, without diluting it, into a thermostatically controlled and stirred reactor.

Taking into account the slight dilution resulting from the removal of the sodium salt of anthraquinone-2-monosulphonic acid, the sugar content of this syrup, on a dry basis, rises to approximately 38%.

This syrup is brought to a temperature of 45° C. and then 50 g of TEMPO and 58 l of bleach with a chlorimetric value of 48°, in the form of a solution diluted beforehand to 25% and adjusted to pH 10.4, are added thereto.

The reaction is allowed to take place at a temperature of 45° C. while continuously adding a 10% sodium hydroxide solution thereto, so as to maintain the pH at 10.4.

After 90 minutes, it is found that sodium hydroxide consumption has become virtually zero.

The contents of the reactor are then percolated through a column of granular activated charcoal, so as to remove the catalyst therefrom, and then this column is eluted with water.

Virtually all the inorganic salts present in this solution are removed by an ion exclusion technique employing strong cationic resins.

The product obtained was then concentrated under vacuum and then dehydrated by spraying. It provided a white powder of glucuronyl arabinarates.

This powder was used as a substitute for polyacrylates in a detergent formula in the proportion of 1 part of glucuronyl arabinarates, thus enriched, per one part of polyacrylates.

The powders obtained not only do not colour on storage but they exhibit highly advantageous detergent qualities since, after having carried out 25 consecutive washes of samples of cotton and cotton/polyester fabrics, the indices of whiteness obtained proved to be greater than the polyacrylate control.

In addition, the level of organic incrustations proves to be significantly lower.

I claim:

1. Process for the alkaline oxidation in aqueous medium, at a pH of approximately 9 to 13, of sugars possessing one or more primary alcohol functional groups using hypohalites in the presence of a catalyst composed of a binary or tertiary alkyl nitroxyl, wherein the concentration of sugars in the aqueous medium is greater than 50 g/l and the reaction temperature is between 30° C. and about 60° C.

2. Process according to claim 1, wherein the catalyst is 2,2,6,6-tetramethylpiperedin-1-oxyl.

3. Process according to claim 1, wherein the sugars are monomers, dimers, trimers and tetramers of simple sugars and wherein the oxidation is performed in the absence of a cooxidizing agent, using sodium hypochlorite as hypohalite.

4. Process according to claim 1, wherein the concentration of sugars in the aqueous medium is greater than 100 g/l.

5. Process according to claim 1, wherein the concentration of sugars in the aqueous medium is greater than 200 g/l.

6. Process according to claim 1, wherein the oxidation is carried out at a temperature greater than 40° C.

7. Process according to claim 3, wherein the oxidation is performed with hypochlorite in the absence of sodium bromide.

8. Glucuronyl-α-(1→4)-glucaric acid.

9. Glucuronyl glucarates containing less than 0.5% of reducing sugars.

* * * * *